United States Patent [19]

Cotterman et al.

[11] Patent Number: 5,157,183

[45] Date of Patent: Oct. 20, 1992

[54] AROMATIZATION PROCESS USING AN IMPROVED CATALYST

[76] Inventors: Ronald L. Cotterman, 8691 Doves Fly Way, Laurel, Md. 20723; David M. Chapman, 10327 Pine Ridge Dr., Ellicott City, Md. 21043

[21] Appl. No.: 625,272

[22] Filed: Dec. 10, 1990

[51] Int. Cl.$^5$ .............................................. C07C 2/52
[52] U.S. Cl. .................................... 585/419; 585/418
[58] Field of Search ............................... 585/418, 419

[56] References Cited

U.S. PATENT DOCUMENTS

| | | | |
|---|---|---|---|
| 3,702,886 | 11/1972 | Arqauer et al. | 423/328 |
| 3,709,979 | 1/1973 | Clu | 423/328 |
| 4,229,282 | 10/1980 | Peters et al. | 208/111 |
| 4,347,394 | 8/1982 | Detz et al. | 585/419 |
| 4,377,503 | 3/1983 | Dessau | 252/455 Z |
| 4,429,176 | 1/1984 | Chester et al. | 585/481 |
| 4,517,395 | 5/1985 | Hoek et al. | 585/415 |
| 4,522,929 | 6/1985 | Chester et al. | 502/77 |
| 4,543,347 | 9/1985 | Heyward et al. | 512/61 |
| 4,551,438 | 11/1985 | Miller | 502/62 |
| 4,559,314 | 12/1985 | Shihaki | 502/71 |
| 4,608,450 | 8/1986 | Miller . | |
| 4,642,176 | 2/1987 | Adams et al. . | |
| 4,652,360 | 3/1987 | Dessau . | |
| 4,717,782 | 1/1988 | Garwood et al. . | |
| 4,740,645 | 4/1988 | Garwood et al. . | |
| 4,766,265 | 8/1988 | Desmond et al. . | |
| 4,816,538 | 3/1989 | Abdo . | |

FOREIGN PATENT DOCUMENTS 0186479  12/1985  European Pat. Off. .

OTHER PUBLICATIONS

"Synthesis of High-Silica Aluminosilicate Zeolites" Studies in Surface Science and Catalysis, vol. 33, Elsevier, New York, N.Y., 1987, Jacobs, P. A., and Martens, J. A., Chapter IV, p. 47.

"Catalysis Today", 6(3), 1990, p. 351–371.

*Primary Examiner*—Asok Pal
*Assistant Examiner*—P. Achutamurthy
*Attorney, Agent, or Firm*—Edward J. Cabic

[57] ABSTRACT

A catalytic process for converting low molecular weight non-aromatic compounds into higher molecular weight aromatic compounds utilizes a unique zeolite catalyst with improved hydrocarbon conversion. The catalyst is a crystalline aluminosilicate having a $SiO_2/Al_2O_3$ ratio greater than 5 and preferably a MFI or MEL zeolite. The zeolite contains a Group VIIIA metal, preferably nickel, and is subjected to thermal or hydrothermal treatments under controlled conditions of temperature, time or steam partial pressure so as to effect a decrease in the amount of carbon deposited as the zeolite catalyst. The catalyst can be used in a process for the conversion of light hydrocarbon feedstocks to improve aromatization activity.

7 Claims, No Drawings

AROMATIZATION PROCESS USING AN IMPROVED CATALYST

CROSS-REFERENCE TO RELATED CASE

This invention utilizes a unique catalyst which is described in U.S. application Ser. No. 449,656, filed Dec. 11, 1989.

BACKGROUND OF THE INVENTION

1. Field of the Invention

This invention relates to the use of an improved catalyst for producing aromatic hydrocarbons from non-aromatic hydrocarbons.

2. Description of the Previously Published Art

The zeolites ZSM-5 and ZSM-11, first described in U.S. Pat. No. 3,702,886 and U.S. Pat. No. 3,709,979, respectively, have been extensively investigated during recent years. These zeolites have more recently been given the designation MFI and MEL zeolites, respectively, in "Chemical Nomenclature, and Formulation of Compositions of Synthetic and Natural Zeolites" IUPAC yellow booklet, 1978. Together, the materials make up the family of the "pentasil" zeolites as discussed in Jacobs, P. A., and Martens, J. A. "Synthesis of High-Silica Aluminosilicate Zeolites" *Studies in Surface Science and Catalysis, Vol.* 33, Elsevier, New York, N.Y., 1987, Chapter IV. There are several patents which describe compositions involving nickel-containing MFI zeolites. For example, U.S. Pat. No. 4,377,503 teaches that a novel shape-selective catalyst can be prepared by incorporating nickel into zeolites such as MFI zeolite. This patent claims only the method of producing the catalyst, and does not specify use of such a material in an aromatization process. The patent also does not recognize the ability of nickel to improve the activity of aromatization catalysts after hydrothermal treatments. U.S. Pat. No. 4,551,438 describes a catalyst for oligomerizing olefins over Ni-MFI zeolite and a hydrocarbyl aluminum halide. The catalyst of the present invention does not contain a hydrocarbyl aluminum halide. U.S. Pat. No. 4,766,265 relates to a process for the conversion of ethane to liquid aromatic hydrocarbons using a gallium modified MFI zeolite promoted with rhenium and nickel. The catalysts of the present invention do not contain gallium or rhenium. U.S. Pat. No. 4,543,347 relates to a catalyst for the conversion of synthesis gas to hydrocarbons using a catalyst that is a mixture of zinc oxide, an oxide of gallium or indium, and possibly nickel supported on MFI zeolite. The composition of the present invention, however, does not contain zinc or gallium or indium.

There are a number of processes for the conversion of hydrocarbons using Ni supported on MFI or MEL zeolites that have been claimed previously. Many of these processes using Ni-MFI and Ni-MEL zeolites are distinctly different from the process of the present invention, the aromatization of non-aromatic hydrocarbons. The use of Ni-MFI and Ni-MEL zeolites for the cracking of paraffinic feedstocks is described in the related case U.S. application Ser. No. 449,656, filed Dec. 11, 1989. Two patents, U.S. Pat. No. 4,229,282 and U.S. Pat. No. 4,642,176 describe dewaxing processes using MFI zeolite with a nickel component. These dewaxing processes are fundamentally different from the aromatization process of the instant invention because they use a feedstock, a hydrocarbon oil, that boils above 350° F. (177° C.) instead of the light gas (C1–C5 hydrocarbon) feedstock of the present invention. Furthermore, the dewaxing processes generally operate at elevated pressures of from 200 to 2000 psig (1.38 to 13.3 MPa) in the presence of hydrogen. U.S. Pat. No. 4,816,538 describes a hydrocracking process for producing high octane gasoline using nickel on zeolites such as MFI zeolite. This hydrocracking process is fundamentally different from the aromatization process of the instant invention because it uses a feedstock, a hydrocarbon oil, that boils above 550° C., which is different from the light gas feedstock of the present invention. Furthermore, the hydrocracking process usually involves reaction at high pressures 1000 to 3000 psig (6.89 to 20.67 MPa) in the presence of hydrogen. There are several patents which describe processes for the conversion of light hydrocarbons, usually C1 to C5 hydrocarbons, to higher boiling hydrocarbons such as C5 to C12 hydrocarbons using nickel containing MFI catalysts. For example, U.S. Pat. No. 4,517,396 claims a process for converting C2 to C5 olefins into middle distillates over Ni-MFI. The process claimed involves reaction at temperatures of 150°–300° C., preferably 175°–250° C. Furthermore, the middle distillate process produces hydrocarbon oil mixtures that boil between 140° C. and 370° C., which is a higher boiling range than the products produced in the present invention. U.S. Pat. No. 4,608,450 reveals technology for a two-stage process for preparing C3 or C4 olefin tetramers using nickel-containing MFI. The process claimed involves reaction at higher pressures, e.g., 200 to 1600 psig (1.38 to 11.03 MPa), and lower temperatures, e.g., 80°–450° F. (27°–232° C.), than the process of the present invention. Furthermore, the process is not intended to produce aromatic hydrocarbons as is the process of the present invention. Finally, the process of the present invention involves reaction of the feedstock in one stage and thus is not a two-stage process for reaction of the feedstock as is the prior art. Thus, the prior art processes are distinctly different from the process of the present invention.

Several patents describe the aromatization of hydrocarbons using Ni on MFI or MEL zeolites. For example, U.S. Pat. No. 4,652,360 assigned to Mobil Oil, U.S. Pat. No. 4,347,394, assigned to Chevron, and EP 186,479 assigned to Mobil Oil, describe base-exchanged (Group IA or IIA metal component) zeolite catalysts having a Group VIII metal component for the aromatization of reformate feedstocks. The acid-catalyzed cracking activity of such catalysts is intentionally minimized by the addition of Group IA and/or Group IIA cations. Thus, the technology practiced in these patents differs from that of the present invention in that the catalyst of the instant invention is maintained in its acidic, or protic, form.

U.S. Pat. No. 4,717,782 and U.S. Pat. No. 4,740,645 assigned to Mobil Oil, disclose using a nickel containing MFI catalyst to oligomerize ethene in the presence of a reducing component such as hydrogen and a co-feed of water. The water is present in an amount to maintain the nickel component of the oligomerization catalyst in an oxidized state. Once the water co-feed is terminated, the Ni-MFI catalyst loses its selectivity advantages. This technology is significantly different from the present invention, however, in that the process of the instant invention does not require the continuous addition of water. Furthermore, the Ni-MFI of the present invention does not lose its activity benefits in the absence of water as a co-feed.

Mild steaming of shape-selective zeolites has been disclosed by Chester et al. in U.S. Pat. Nos. 4,429,176 and 4,522,929, as enhancing both the alpha activity and stability of such catalysts in acid-catalyzed reactions such as xylene isomerization. U.S. Pat. No. 4,559,314 to Shihabi, teaches that very highly siliceous shape-selective selective zeolites, which are inactive, can be activated by steaming the alumina bound zeolite. However, these patents do not recognize that nickel improves the activity of MFI zeolite after severe thermal or hydrothermal treatment.

3. Objects of the Invention

It is an object of this invention to convert non-aromatic compounds into aromatic compounds with a catalyst containing an acidic crystalline zeolite material and a Group VIIIA metal functionality.

It is a further object of this invention to produce aromatic hydrocarbons from non-aromatic compounds with a catalyst that maintains high activity after severe thermal and hydrothermal treatments such as are encountered in regeneration steps in processes for producing aromatic hydrocarbons.

These and further objects will become apparent as the description of the invention proceeds.

SUMMARY OF THE INVENTION

This invention provides a process for producing aromatic hydrocarbons from non-aromatic compounds with a catalyst comprising a crystalline zeolite material such as an MFI-type or MEL-type zeolite, wherein the zeolite is promoted with nickel metal. Such a nickel promoted zeolite has improved activity retention relative to the material without nickel for the aromatization of light gases such as propane, propylene and their mixtures after the catalyst has been given a severe hydrothermal treatment. Since severe hydrothermal treatments occur during the regeneration of coked catalyst, the nickel containing catalyst of the present invention is expected to exhibit enhanced activity in processes which require catalyst regeneration.

DESCRIPTION OF THE PREFERRED EMBODIMENTS

The term zeolite as used herein refers to microporous structures of silicates or aluminosilicates. The zeolites have crystalline, hydrated frameworks, based on a three dimensional network of $SiO_4$ tetrahedra possibly with $AlO_4$ tetrahedra, wherein the tetrahedra are linked to each other by the sharing of oxygens. Exemplary of these materials are Zeolite ZSM-5 (U.S. Pat. No. 3,702,886) and Zeolite ZSM-11 (U.S. Pat. No. 3,709,979).

Zeolites are best characterized according to framework structure type, i.e., on the topology of the framework, irrespective of composition, distribution of different tetrahedral atoms, cell dimensions and symmetry. A code consisting of three capital letters has been adopted for each known structure type following the recommendations by IUPAC on zeolite nomenclature ("Chemical Nomenclature, and Formulation of Compositions of Synthetic and Natural Zeolites" IUPAC yellow booklet, 1978) and a compilation of 38 known zeolite structure types has been published by The Structure Commission of the International Zeolite Association ("Atlas of Zeolite Structure Types", by Meier, W. and Olson, D. H. (1978)). The structure types that are pertinent to the present invention are the MFI (ZSM-5) and MEL (ZSM-11) structures.

The $SiO_2/Al_2O_3$ molar ratio of the zeolites of the present invention is in the range of about 5:1 to about 500:1, preferably ranging from about 20:1 to about 100:1. The preparation of the preferred zeolites used in the present invention is described in copending application Ser. No. 449,656, filed Dec. 11, 1989, the entire contents of which are incorporated herein by reference. The as-synthesized zeolite can contain organic and/or alkali metal cations which are removed prior to catalytic use. The organic cations can be effectively removed during a calcination of the zeolite, at a temperature of between about 300° C. and 700° C., preferably between about 400° C. and 600° C., for a period of from about 1 hour to about a few days. The alkali metal cations can be effectively removed by ion exchange, such as by treatment of the zeolite with a strong acid, and/or by ion exchange with other cations such as ammonium cation. In one embodiment, the zeolite in as-synthesized form is exchanged with ammonium ions, calcined at 550° C. in air for 1 hour, followed by a second ammonium ion exchange. These treatments replace the extra framework cations with ammonium cations. The ammonium form of the zeolite can then be calcined to generate the acid form of the zeolite.

The zeolite, usually in its ammonium ($NH_4$) or the acid (H) form is given a treatment with a source of a nickel metal. The term "treatment" refers to ion exchange, impregnation or any other known method of incorporating the metal into the zeolite. The preferred method of metal incorporation uses, but is not limited to, in the case of nickel to water soluble nickel salts with Ni in the 2+ valence state such as $Ni(NO_3)_2$ or $NiCl_2$. The nickel on the zeolite may be present in an amount from about 0.1 wt % Ni to about 10 wt % Ni of the total weight of the zeolite. The preferred metal content of the zeolite is from about 0.3 wt % to about 5 wt %.

A binder may be added to aid in fabricating the zeolite catalyst into a suitable form. Binder materials which may be used include clays, alumina, silica, aluminophosphate and other suitable oxide materials. The finished catalyst may contain binder amounts of between zero and about 95% by weight, more preferably between about 10% and about 50% by weight. The preferred binder material is silica, which can be incorporated in colloidal form from materials such as Ludox AS-40, available from DuPont. Silica has been found not to interfere with catalyst activity and additionally does not promote side reactions, such as coking.

Once the zeolite is in its ammonium or protic form and contains the added metal such as nickel, and either before or after the zeolite is bound into a formulated catalyst with a binder material, the zeolite is activated with a thermal or hydrothermal treatment. Catalysts prepared in the above manner have a high initial activity, but this may decline rapidly because of an accompanying high rate of carbon deposition. However, it has been found that the catalyst can initially be partially deactivated so that the carbon deposition is significantly reduced with only a small effect on activity. This controlled deactivation may be produced by treating the catalyst with steam or by a high temperature dry calcination. The thermal or hydrothermal treatment may also be carried out as part of a regeneration procedure on a catalyst which has been partially or wholly deactivated in use.

The thermal treatment in any of the above embodiments is suitably carried out by heating the material in an oxidizing atmosphere such as air. The thermal treatment should be carried out at temperatures of between about 400° C. and 1000° C., preferably between about 500° C. and 800° C., for periods of time ranging from about 0.5 hours to a few days, preferably about 1 hour. Increasing the severity of one or more relevant parameters may allow reduction of the severity of other relevant parameters. For instance, raising the thermal treatment temperatures can be expected to shorten the duration of the treatment needed to improve the activity of the zeolite.

Similarly, the hydrothermal treatment in any of the above embodiments is suitably carried out by heating the material in an atmosphere containing steam as such or a carrier gas stream comprising steam. The carrier gas stream used for steam treatment suitably contains a partial pressure of steam from about 1% to about 100%. The carrier gas stream may contain air, nitrogen or any other inert gas. The hydrothermal treatment is suitably carried out at a pressure of between 0.01 and 1.0 MPa (1 to 145 psi), preferably at about 0.1 MPa, and a temperature between about 400° C. and 900° C., preferably between about 500° C. and 800° C. The hydrothermal treatment should be carried out for periods of time ranging from about 0.5 hours to a few days, preferably about 1 hour to about 8 hours. Increasing the severity of one or more relevant parameters may allow reduction of the severity of other relevant parameters. For instance, raising the hydrothermal treatment temperature can be expected to shorten the duration of the treatment needed to improve the catalytic activity of the zeolite.

The pretreatment conditions have a distinct influence on the distributions of hydrocarbon products observed in the tetradecane cracking reaction when compared at constant conversion. an increase in the thermal pretreatment temperature from 550° C. to 750° C. results in a decrease in the paraffin content of the gasoline range product as well as in the yields of C4 and C5 paraffins. Under these preferred conditions, the cracking of tetradecane at 500° C., atmospheric pressure and 55% conversion produces an n-paraffin selectivity in the C5-C12 fraction of the products which is less than 29 wt. %. Furthermore, the C4 and C5 paraffin/olefin ratios decrease with increasing thermal pretreatment temperature, while the calculated research and motor octane numbers of the gasoline range product increase.

Similar trends are observed for the hydrothermally treated samples. An increase in the hydrothermal pretreatment temperature from 550° C. to 750° C. results in a decrease in the paraffin content of the gasoline range product as well as in the yields of C4 and C5 paraffins. Furthermore, the C4 and C5 paraffin/olefin ratios decrease with increasing hydrothermal pretreatment temperature, while the calculated research and motor octange number of the gasoline range product increase.

This thermal or hydrothermal treatment affects a transformation of the predominant x-ray photoelectron spectral feature of the nickel metal. This transformation is discussed further in U.S. application Ser. No. 449,656, filed Dec. 11, 1989, the entire contents of which are incorporated herein by reference. The transformation of the predominant x-ray photoelectron spectral feature involves the transformation of the Ni 2p feature from one with a line shape and binding energy similar to those of NiO to one with a line shape and binding energy similar to those of $NiAl_2O_4$. The hydrothermal treatment causes the catalyst to have an increase in the relative surface concentrations of nickel and aluminum in the zeolite.

The process of the present invention relates to the conversion of light gases to liquid aromatic hydrocarbons. Suitable light gases are ethane, ethene, propane, propene, butanes, butenes, pentanes and pentenes, either used individually or as mixtures. The conversion of the light gases is accomplished by contacting a hydrocarbon feedstock rich in the suitable light gas components with a catalyst prepared according to the present invention. Non-deleterious components, such as inert gases, may also be present.

An example of such an aromatization process is the Cyclar process (*Hydrocarbon Processing*, Sep. 1989, p. 72). This process uses liquified petroleum gas (LPG) as a feedstock and converts the propane and butanes of LPG to aromatics. The aromatics produced in the present process are composed mostly of benzene, toluene, and xylenes with a small amount of C9 and heavier aromatics. These products boil in the range 92° C. to 210° C.

The temperature of the reactor for the hydrocarbon conversion ranges from about 100° C. to about 700° C., and the pressure of the reaction is about 0.1 MPa (1 atm, 0 psig) to about 10 MPa (100 atm, 1500 psig). The preferred temperature of the reaction is in the range of 400° C. to 600° C., and the preferred pressure of the reaction is 0.1 MPa (1 atm, 0 psig) to 2 MPa (20 atm, 300 psig).

Upon being exposed to the reaction conditions over a period of time, the catalyst gradually accumulates a certain level of coke. If left untreated, the progressive coke buildup eventually leads to the deactivation of the catalyst. In the reactor design, catalyst that is still active, but which has some coke buildup is slowly withdrawn from the bottom of the last reactor stage and transferred to the regeneration section while an equivalent volume of regenerated catalyst is conveyed from the regenerator back to the top of the first reactor. Regeneration consists of the combustion of the deposited coke using high temperature air and/or steam.

After many such regeneration cycles, catalyst activity can decay from thermal degradation of the catalyst. The present invention provides a catalyst which retains a greater portion of its original activity even after very severe hydrothermal treatments.

Having described the basic aspects of our invention, the following examples are given to illustrate specific embodiments thereof. As is known in the art, and set forth in "Catalysis Today", 6(3), 1990, p. 351-371, MFI and Ga-MFI zeolites are useful for the aromatization of light gases. Thus, we describe the preparation and evaluation of these materials in comparison examples.

EXAMPLE 1

This example describes the preparation of an MFI-type zeolite.

An MFI-type zeolite was crystallized according to Jacobs, P. A., and Martens, J. A. "Synthesis of High-Silica Aluminosilicate Zeolites" *Studies in Surface Science and Catalysis, Vol.* 33, Elsevier, New York, N.Y., 1987, pg. 47. Chemical analysis of the product showed that on an anhydrous basis the product contained 2.4 wt % $Na_2O$, 3.7 wt % $Al_2O_3$ and 93.9 wt % $SiO_2$. The crystallite size averaged about 0.2 micron. The surface area was 405 $m^2/gm$. A 200 gm portion of this crystalline product was slurried in 2 L of 1N $NH_4NO_3$ solution and heated at 80° C. for 1 hour. The product was filtered and washed with deionized water. It was then ramped in air at 2° C./min to 550° C. and held for 1 hour. The sample was cooled slowly to ambient temperature and was then slurried again in 2 L of 1N $NH_4NO_3$ and heated at 80° C. for 1 hour. The product was filtered and washed with deionized water and dried at 100° C. overnight. Chemical analyses of the product showed that the $Na_2O$ level was 0.025 wt %, on an anhydrous basis.

EXAMPLE 2

This example describes the preparation of a Ni-MFI zeolite used in subsequent examples.

Thirty two gms, on an anhydrous basis, of the product of Example 1 were impregnated with a solution consisting of 3.90 gms $Ni(NO_3)_2.6H_2O$ in 28 ml water. The product was dried at 100° C., and then ramped in air at 2° C./min to 400° C., and was held at that temperature for 1 hour. It was then cooled slowly to ambient temperature. The product contained 0.025% $Na_2O$ and 2.27% Ni on an anhydrous basis.

EXAMPLE 3

This example describes the preparation of a catalytically active Ni-MFI zeolite thermally treated at 550° C. in air.

Six gms of the product from Example 2 were ramped in air at 2° C./min to 550° C., and were held at that temperature for 1 hour. The sample was then cooled slowly to ambient temperature.

EXAMPLE 4

This example describes the preparation of a catalytically active Ni-MFI zeolite hydrothermally treated at 750° C.

Six gms of the product from Example 2 were meshed −14 +25, and were then ramped under flowing nitrogen to 750° C. over the period of 1 hour. The sample was held at that temperature for 4 hours while a mixture of 95% water/5% nitrogen was passed over the zeolite at atmospheric pressure. The product was then cooled slowly to ambient temperature.

COMPARISON EXAMPLE 1

This example describes the preparation of a catalytically active MFI zeolite thermally treated at 550° C. in air. This serves as a comparison because there is no Ni present.

Six gms of the product from Example 1 were ramped in air at 2° C./min to 550° C., and were held at that temperature for 1 hour. The sample was then cooled slowly to ambient temperature.

COMPARISON EXAMPLE 2

This example describes the preparation of a catalytically active MFI zeolite hydrothermally treated at 750° C. This serves as a comparison because there is no Ni present.

Six gms of the product from Example 1 were meshed −14 +25, and were then ramped under flowing nitrogen to 750° C. over the period of 1 hour. The sample was held at that temperature for 4 hours while a mixture of 95% water/5% nitrogen was passed over the zeolite at atmospheric pressure. The product was then cooled slowly to ambient temperature.

COMPARISON EXAMPLE 3

This example describes the preparation of a catalytically active Ga-MFI zeolite which will be used for comparison.

Thirty gms, on an anhydrous basis, of the product of Example 1 were impregnated with a solution consisting of 0.9 gms of $Ga(NO_3)_3$ in 27 ml water. The product was then ramped in air at 2° C./min to 550° C., and was held at that temperature for 1 hour. It was then cooled slowly to ambient temperature. The product contained 0.57 wt % Ga on an anhydrous basis.

COMPARISON EXAMPLE 4

This example describes the preparation of a hydrothermally treated Ga-MFI-type zeolite which will be used for comparison.

A small portion of the product from Comparison Example 3 above, meshed −14 +25, was ramped under flowing nitrogen to 750° C. over the period of 1 hour. It was held at this temperature for 4 hours while a mixture of 95% water/5% nitrogen was passed over the zeolite at atmospheric pressure. The product was then cooled slowly to ambient temperature.

EXAMPLE 5

This example describes the comparison testing of catalysts for the conversion of propane/propene into aromatics.

Catalysts from Comparison Examples 1-4 and Examples 3-4 were tested individually under identical conditions in an isothermal, tubular reactor. Catalyst materials were evaluated for catalytic activity and selectivity in the following way. A 1.0 gram quantity of 40/80 meshed catalyst, mixed with glass beads, was heated to 500° C. in a stainless steel tube (i.d. 7.8 mm). 2.1 g/hour of a 50/50 blend of propane and propene were passed through the catalyst bed at atmospheric pressure. Reaction products were sampled after 3 min on stream and analyzed by gas chromatography. The results of these tests are shown in Table 1.

TABLE 1

| DESCRIPTION | EXAMPLE | WHSV (hr$^{-1}$) | Conv. (wt %) | Aromatics Yield (wt %) |
|---|---|---|---|---|
| Calcined @ 550° C. | | | | |
| Ni-MFI | 3 | 2.1 | 83.0 | 18.2 |
| Ga-MFI | CE3 | 2.1 | 76.6 | 17.9 |
| MFI | CE1 | 2.1 | 60.7 | 20.3 |
| Steamed @ 750° C. | | | | |
| Ni-MFI | 4 | 2.1 | 50.5 | 23.8 |
| Ga-MFI | CE4 | 2.1 | 39.1 | 9.2 |
| MFI | CE2 | 2.1 | 24.7 | 3.7 |

The results shown in Table 1 clearly demonstrate the advantage of using Ni-MFI as a catalyst for the conversion of propane/propene into aromatics. The activity of Ni-MFI is much higher than that of either MFI or Ga-MFI materials with similar thermal or hydrothermal pretreatment. Furthermore, the aromatics yield over Ni-MFI is much higher than those for Ga-MFI or MFI after 750° C. steam treatment.

EXAMPLE 6

This example describes the properties of an MEL zeolite.

A sample of MEL zeolite in its protic form was received from the Georgia Tech Research Institute. The sample was distinguished from the MFI-type zeolites by the absence of a diffraction line at 9.06° 2-theta according to Jacobs, P. A. and Martens, J. A. "Synthesis of High Silica Aluminosilicate Zeolites", *Studies in Surface Science and Catalysis*. Vol. 33, Elsevier, New York, 1987. Chemical analysis of the product indicated that on an anhydrous basis the product contained 95.3 wt % $SiO_2$, 4.72 wt % $Al_2O_3$ and 0.022 wt % $Na_2O$.

EXAMPLE 7

This example describes the preparation of a hydrothermally treated, catalytically active Ni-MEL zeolite.

Five gms, on an anhydrous basis, of the MEL zeolite described in Example 6 were impregnated with a solution consisting of 0.62 gms $Ni(NO_3)_2.6H_2O$ in 3 ml water. The product was dried at 100° C., and then ramped in air at 2° C./min to 550° C., and was held at that temperature for 1 hour. It was then cooled slowly to ambient temperature. The product contained 2.56% Ni on an anhydrous basis. The sample was then meshed −14 +25 and was ramped under flowing nitrogen to 750° C. over the period of 1 hour. It was held at that temperature for 4 hours while a mixture of 95% water/5% nitrogen was passed over the zeolite at atmospheric pressure. The product was then cooled slowly to ambient temperature.

COMPARISON EXAMPLE 5

This example describes the preparation of a hydrothermally treated, catalytically active MEL zeolite which will be used for comparison.

A portion of the sample from Example 6 was meshed −14 +25 and then was ramped under flowing nitrogen to 750° C. over the period of 1 hour. It was held at that temperature for 4 hours while a mixture of 95% water/5% nitrogen was passed over the zeolite at atmospheric pressure. The product was then cooled slowly to ambient temperature.

EXAMPLE 8

This example describes the comparison testing of catalysts for the conversion of a mixture of propane/propene into aromatics.

Catalysts from Comparison Example 5 and Example 7 were tested individually using a 50/50 blend of propane and propene as feed that was fed at 2.1 g/hour. All other conditions were identical as those described in Example 5. The results of these tests are shown in Table 2.

TABLE 2

| DESCRIPTION | EXAMPLE | WHSV (hr$^{-1}$) | Conv. (wt %) | Aromatics Yield (wt %) |
|---|---|---|---|---|
| Steamed @ 750° C. | | | | |
| Ni-MEL | 7 | 2.1 | 45.5 | 24.3 |
| MEL | CE5 | 2.1 | 33.8 | 7.1 |

The results in Table 2 clearly demonstrate the activity advantage of using Ni-MEL as a catalyst for conversion of propane and propene into aromatics. The activity is significantly higher for Ni-MEL compared to MEL after identical hydrothermal pretreatment. Furthermore, the aromatics yield for Ni-MEL is greater than that for MEL zeolite.

It is understood that the foregoing detailed description is given merely by way of illustration and that many variations may be made therein without departing from the spirit of this invention.

What is claimed is:

1. A catalytic process for converting low molecular weight non-aromatic compounds into higher molecular weight aromatic compounds comprising contacting the non-aromatic compounds, having at least 2 carbon atoms, at an elevated temperature of about 100° C. to 700° C. and pressure of about 0.1 MPa to 10 MPa with an aromatic conversion catalyst comprising a crystalline aluminosilicate zeolite in its protic (acidic) form, having a $SiO_2/Al_2O_3$ ratio greater than 5, and containing nickel, and having been subjected to severe hydrothermal treatment under controlled conditions of temperature, time or steam partial pressure and at a temperature of at least 500° C. so that a) the Ni 2p x-ray photoelectron spectra; feature is transformed from one with a line shape and binding energy similar to those of NiO to one with a line shape and binding energy similar to those of $NiAl_2O_4$; and b) the n-paraffin selectivity of the C5 to C12 fraction of products produced during the cracking of n-tetradecane at 500° C., 1 atmosphere and 55% conversion is less than 29 wt %.

2. A catalytic process according to claim 1, wherein the non-aromatic compound is selected from the group consisting of ethane, ethene, propane, propene, butanes, butenes, pentanes, pentenes and mixtures thereof.

3. A catalytic process according to claim 1, wherein said zeolite is an MFI zeolite.

4. A catalytic process according to claim 1, wherein said zeolite is an MEL zeolite.

5. A catalytic process according to claim 4, wherein the Ni is present from about 0.1 wt % to 10 wt % of the total weight of the zeolite.

6. A catalytic process according to claim 5, wherein the Ni is present from about 0.3 wt % to 5 wt % of the total weight of the zeolite.

7. A catalytic process according to claim 1, wherein said zeolite has a $SiO_2/Al_2O_3$ ratio greater than 5 to about 200.

* * * * *

UNITED STATES PATENT AND TRADEMARK OFFICE
CERTIFICATE OF CORRECTION

PATENT NO. : 5,157,183
DATED : October 20, 1992
INVENTOR(S) : Cotterman et al It is certified that error appears in the above-identified patent and that said Letters Patent is hereby corrected as shown below:

Column 10, line 33, change "spectra;" to "spectral".

Signed and Sealed this

Twelfth Day of October, 1993

Attest:

BRUCE LEHMAN

*Attesting Officer*         *Commissioner of Patents and Trademarks*